(12) United States Patent
Forat et al.

(10) Patent No.: US 6,464,895 B2
(45) Date of Patent: *Oct. 15, 2002

(54) REAGENT AND PROCESS WHICH ARE USEFUL FOR GRAFTING A SUBSTITUTED DIFLUOROMETHYL GROUP ONTO A COMPOUND CONTAINING AT LEAST ONE ELECTROPHILIC FUNCTION

(75) Inventors: Gérard Forat, Lyons (FR); Jean-Manuel Mas, Millery (FR); Laurent Saint-Jalmes, Meyzieu (FR)

(73) Assignee: Rhodia Chimie, Courbevoie Cedex (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/201,854

(22) Filed: Dec. 1, 1998

(65) Prior Publication Data

US 2002/0042542 A1 Apr. 11, 2002

Related U.S. Application Data

(60) Continuation-in-part of application No. 09/012,232, filed on Jan. 23, 1998, now abandoned, and a continuation-in-part of application No. 08/620,359, filed on Mar. 22, 1996, now Pat. No. 5,859,288, said application No. 09/012,232, is a division of application No. 08/620,348, filed on Mar. 22, 1996, now Pat. No. 5,756,849.

(30) Foreign Application Priority Data

| Mar. 24, 1995 | (FR) | 95 03512 |
| Dec. 29, 1995 | (FR) | 95 15763 |
| Dec. 29, 1995 | (FR) | 95 15764 |

(51) Int. Cl.[7] ............... C07D 53/18; C09K 15/06
(52) U.S. Cl. ................. 252/182.12; 562/605
(58) Field of Search .......... 252/182.12; 558/605; 562/605

(56) References Cited

U.S. PATENT DOCUMENTS

| 4,808,748 A | * | 2/1989 | Lin et al. ............ 558/378 |
| 4,814,480 A | * | 3/1989 | Davidson ............ 558/378 |
| 4,990,699 A | * | 2/1991 | Stahly ............ 568/933 |

FOREIGN PATENT DOCUMENTS

| EP | 165135 | | 12/1985 |
| EP | 307519 | | 3/1989 |
| FR | 2593808 | | 8/1987 |
| FR | 2660923 | | 10/1991 |
| JP | 4-193856 | * | 7/1992 |

OTHER PUBLICATIONS

Marc Tordeaux et al., *Reactions of Trifluoromethyl Bromide and Related Halides: Part 9. Comparison Between Additions to Carbonyl Compounds, Enamines, and Suphur Dioxide in the Presence of Zinc,* Journal of the Chemical Society, No. 7, Jul. 1990, pp. 1951–1957.
Marc Tordeaux et al., *Reactions of Bromotrifluromethane and Related Halides. 8. Condensations with Dithionite and Hydroxymethanesulfinate Salts,* Journal of Org. Chem., 1989, 54, 2452–2453.
G. Patrick Stahly, *Trifluromethylation of 1,3,5–Trinitobenzene,* Journal of Fluorine Chemistry, 45 (1989) 431–433.

* cited by examiner

Primary Examiner—Joseph K. McKane
Assistant Examiner—Rebecca Anderson
(74) Attorney, Agent, or Firm—Burns, Doane, Swecker & Mathis, L.L.P.

(57) ABSTRACT

The invention relates to a nucleophilic reagent which is useful for grafting a substituted difluoromethyl group onto a compound containing at least one electrophilic function, or for the synthesis of oxysulphide-containing and fluorine-containing organic derivatives, wherein said reagent comprises:

a) a fluorocarboxylic acid of formula Ew—$CF_2$—COOH where Ew represents an electron-withdrawing atom or group, at least partially salified with an organic or inorganic cation, and
b) a polar aprotic solvent;
and in that the content of releasable protons carried by its various components, including their impurities, is at most equal to half the initial molar concentration of the said fluorocarboxylic acid.

A synthetic process uses this reagent by heating in order to graft a substituted difluoromethyl group onto various compounds.

17 Claims, No Drawings

REAGENT AND PROCESS WHICH ARE USEFUL FOR GRAFTING A SUBSTITUTED DIFLUOROMETHYL GROUP ONTO A COMPOUND CONTAINING AT LEAST ONE ELECTROPHILIC FUNCTION

This application is a continuation-in-part of application Ser. No. 08/620,359, filed Mar. 22, 1996, now U.S. Pat. No. 5,859,288, and of application Ser. No. 09/012,232 filed Jan. 23, 1998, now abandoned, which is a divisional application of application Ser. No. 08/620,348 filed Mar. 22, 1996, now U.S. Pat. No. 5,756,849. The contents of each of the above-mentioned applications are hereby incorporated by reference.

The present invention relates to a reagent and a process for grafting a substituted difluoromethyl group onto a compound containing at least one electrophilic function. The invention relates more particularly to a technique for perfluoroalkylating various compounds by nucleophilic substitution reactions or addition reactions typically performed by organometallic derivatives.

The present invention further relates to a process for the preparation of fluoroalkanesulphinic and sulphonic acids and their salts.

It relates more particularly to the preparation of polyhalosulphinic and sulphonic, especially difluoro- or trifluoromethanesulphinic and sulphonic, acids.

The techniques of perfluoroalkylation, or equivalent techniques, generally use derivatives of the perfluoroalkyl iodide type, in the presence of zinc. This technique is thus expensive, while at the same time requiring treatment plants for the metallic waste which should be treated, since zinc is a great pollutant of water courses.

The other techniques, in which the perfluoroalkyl radical does not form a stabilized reactive intermediate of the organometallic type, are generally difficult to carry out on account of the very low stability of the free perfluoro anions in the reaction media. These anions generally lead to products of the carbene type, by loss of one of their substituents.

Perhaloalkanesulphonic acids and more particularly trifluoromethanesulphonic acid are used as catalysts or as intermediates in organic synthesis.

Initially, the only known process for the manufacture of trifluoromethanesulphonic acid was electro-chemical fluorination as described especially by R. D. Howels, J. D. McCown in Chemical Reviews, 1977, 77, 69.

The process for the preparation of trifluoromethanesulphinic acid, which is described in the European patent published under the number EP-165 135, is also known which consists in exposing to sulphur dioxide a metal selected from zinc, aluminium, manganese, cadmium, magnesium, tin, iron or even nickel and cobalt, in an aprotic polar solvent and then in adding a trifluoromethyl halide at a pressure greater than $10^5$ Pa. This process makes it possible to obtain a product in the form of trifluoromethanesulphinate with good yields. The sulphinate obtained is present in a medium containing a large quantity of zinc salt. The separation of the sulphinate and the other zinc salts poses, at the industrial level, a problem which has to be solved.

Moreover, this technique, as well as the one described in the French application published under the number 2,593,808, required the use of perfluoroalkyl bromides which are reputed to be particularly harmful for the atmospheric layers, especially because of their high greenhouse effect and their reputedly damaging effect on ozone.

Consequently, one of the aims of the present invention is to provide a reagent which allows a perfluoroalkylation according to a mechanism of the type involving a carbanion, without using organometallic reagents of transition metals such as zinc.

Accordingly, another aim of the present invention is to provide a reagent for the preparation of oxysulphide-containing and fluorine-containing organic derivatives, by reacting with an oxide of sulphur, which makes it possible to use products which are less harmful for the environment than trifluoromethyl bromide while remaining low in price.

It has often been sought to use as a source of perfluoroalkyl radicals, more generally of trifluoromethyl radicals, perfluorocarboxylic acids, by carrying out decomposition reactions aimed at eliminating the carboxylic fragment from the said acids, releasing carbon dioxide. However, the successes which were obtained were very mitigated and used particularly complex catalytic systems. The perfluoroalkyl radicals or equivalents thereof generated by the decomposition of the said perfluorocarboxylic acids were, in addition, unstable in the reaction medium and required the use of stabilizing agents.

G. Stahly has also reported, in Journal of Fluorine Chemistry, 45 (1989), 431–433 and in U.S. Pat. No. 4,990,699, that the thermal decomposition of perfluoroalkanoic salts in the presence of aromatic compounds such as 1,3,5-trinitrobenzene leads to the formation of trifluoromethyl anions $CF_3^-$, demonstrated by the formation of a Meisenheimer complex. The complex may subsequently be converted by oxidation to give the perfluoroalkyl derivative on the corresponding aromatic ring.

However, the need to carry out this oxidation makes this route for the perfluoroalkylation of aromatic derivatives tedious.

The present invention proposes to circumvent the drawbacks of the existing processes by providing a reagent which is non-hazardous to the environment and capable of leading to the desired products in a satisfactory yield.

In the course of the study which led to the present invention, it has been demonstrated that a fluoroalkylation reaction was possible with a fluorocarboxylic acid salt, without a catalyst and without an agent capable of stabilizing the various envisaged intermediates obtained during the decomposition of the various perfluorocarboxylic acids.

It appeared that, in order thus to obtain a decomposition of the fluorocarboxylic acids, two conditions were essential; one is the choice of the solvent, and the other the content of impurities in the mixture constituting the reagent according to the present invention. Thus, it was possible to demonstrate the absolutely critical role of the content of labile hydrogens in the system, or more precisely of releasable protons, which must be less than the content of fluoro groups released by the decomposition of the fluorocarboxylic acid salts. The terms labile hydrogen and releasable proton refer to a hydrogen atom which is capable of being removed out in the form of a proton by a strong base. In practice, these are protons of acidic functions which have a pKa of less than about 20 (by "about", it is emphasized that the number 20 has only one significant figure).

The above-mentioned aims and others, which will appear later, are achieved by means of a nucleophilic reagent which is useful for grafting a substituted difluoromethyl group onto a compound containing at least one electrophilic function, or which is useful for the synthesis of oxysulphide-containing and fluorine-containing organic derivatives by reacting with an oxide of sulphur, especially sulphur dioxide, wherein said reagent comprises:
a) a fluorocarboxylic acid of formula $Ew—CF_2—COOH$ where Ew represents an electron-withdrawing atom or group, at least partially salified with an organic or inorganic cation, and
b) a polar aprotic solvent;
and wherein the content of releasable protons carried by its various components, including their impurities, is at most equal to half the initial molar concentration of the said fluorocarboxylic acid.

The electrophilic functions capable of reacting with the reagent of the present invention are the functions which usually react with organometallic reagents and will be detailed later.

The lower the content of releasable protons in the reagent, the lower the risk of side reactions will be and the better the yield will be.

Thus, it is preferable for the content of labile hydrogen atoms in the reagent to be at most equal to 10%, preferably to 1% (in moles), relative to the initial content of the said fluorocarboxylic acid.

The main impurity, as a carrier of labile hydrogen atoms, is generally water, which is capable of releasing up to two hydrogen atoms per molecule.

In general, it is preferable to use carefully dehydrated reagents and solvents, so that the weight content of water in the reagent is at most equal to 1 per 1000 relative to the total mass of the reagent.

Depending on the overall reaction conditions, such water contents may be satisfactory, but in certain cases, it may be advantageous to work at lower levels, for example of about 1 per 10,000.

However, it is not necessarily essential to remove all of the water and a water/fluorocarboxylic acid molar ratio of less than 10% may be tolerated.

Moreover, it was possible to show that other elements, namely transition elements having two stable valency states, such as copper, may not to be beneficial, and could even be harmful.

Although this reagent according to the invention requires no catalyst, such metal elements may be present as impurities supplied in particular by the solvent.

Thus, it is preferable for the molar content of these elements to be less than 1000, advantageously than 100, and preferably than 10 ppm relative to the initial content of the said fluorocarboxylic acid.

Also, although it has been recommended many times to use elements from column VIII of the Periodic Table of the Elements with perfluoroacetic acid, in order to promote certain substrates and to promote certain types of reaction, this proved to be particularly harmful for the reaction intended above. Consequently, it is preferable to use reagents containing no metals from column VIII, in particular metals of the platinum ore, which is the group consisting of platinum, osmium, iridium, palladium, rhodium and ruthenium.

In the present description, reference is made to the supplement to the Bulletin de la Société Chimique de France No. 1, January 1966, in which a Periodic Table of the Elements was published.

Thus, it is preferable for the content of platinum ore metals, or even of metals from column VIII, to be less than 100 ppm, advantageously than 10 ppm, preferably than 1 ppm. These values are expressed relative to the starting fluorocarboxylic acid and are expressed in moles.

In a more general and more empirical manner, it may be indicated that these two categories of metals, namely transition metals with two valency states and the elements of column VIII, should be present in the reagent at an overall concentration level at most equal to 1000 mol ppm, preferably to 10 mol ppm.

It will be noted that the various metals present at such an overall concentration level are extremely low in quantity and, in this respect, they play no catalytic role. Their presence does not improve the reaction kinetics, or is even harmful thereto when they are present in too large an amount.

The use, in addition to the components of the abovementioned reagents, of alkali metal fluoride or of quaternary ammonium fluoride, which are usually present in the reagent systems using fluorocarboxylates, did not turn out to be harmful, but did prove to be of little value, on account of the fact that it produces saline effluents which are difficult to treat.

It is noted, however, that the presence of fluorides in the medium tends to limit the conversion of the fluorocarboxylic acid, but tends to reduce side reactions.

This effect tends to be greater the bulkier the countercation of the fluoride. Cations which may be envisaged are the cations of alkali metals higher in rank than sodium, in particular potassium or caesium, or alternatively ions of "onium" type, namely cations formed by the elements of columns V B and VI B (as defined in the Periodic Table of the Elements published in the supplement to the Bulletin de la Société Chimique de France in January 1966), with 4 or 3 hydrocarbon chains.

Among the oniums derived from elements of column V B, the preferred reagents are tetraalkyl or tetraaryl ammonium or phosphonium. The hydrocarbon group advantageously contains from 4 to 12 carbon atoms, preferably from 4 to 8 carbon atoms. The oniums derived from column VI B are preferably derived from elements with an atomic number higher than that of oxygen.

Despite the drawbacks which have been mentioned above, the content of fluoride ions is a parameter which may be considered. It may, however, be preferable to limit this content, in particular the initial content, so as to facilitate the final treatment of the reaction medium.

Thus, it is advantageous for the content of fluoride, which is qualified as being ionic, that is to say capable of being ionized in the polarizing medium of the reagent, to be at least equal to the initial molar concentration of the said fluorocarboxylic acid salt, advantageously to a half and preferably to a quarter of this concentration.

As has been mentioned above, the solvent plays an important role in the present invention and must be aprotic and advantageously polar and contain very few impurities carrying acidic hydrogen.

It is thus preferable for the polar aprotic solvent which can be used to have a significant dipolar moment. Thus, its relative dielectric constant e is advantageously at least equal to about 5 (the positional zeros are not considered as being significant figures in the present description unless specified otherwise). Preferably, e is less than or equal to 50 and greater than or equal to 5, and is in particular between 30 and 40.

It is moreover preferred for the solvents of the invention to be capable of fully solvating the cations, which may be classified by the donor number D of these solvents. It is thus preferable for the donor number D of these solvents to be between 10 and 30. The said donor number corresponds to the DH (enthalpy difference), expressed in kilocalories per mole, for the association of the said polar aprotic solvent with antimony pentachloride.

According to the present invention, it is preferable for the reagent to have no acidic hydrogen on the polar solvent or solvents which it uses. In particular, when the polar nature of the solvent or solvents is obtained by the presence of electron-withdrawing groups, it is desirable for there to be no hydrogen alpha to the electron-withdrawing function.

More generally, as for all the components of the reagents, it is preferable for the pKa corresponding to the first acidity of the solvent to be at least equal to about 20 ("about" emphasizing that only the first figure is significant), advantageously at least equal to about 25, preferably between 25 and 35.

The acidic nature may also be expressed by the acceptor number AN of the solvent, as defined by Reichardt in "Solvents and solvent effects in Organic Chemistry", 2nd edition, VCH (RFA), 1990, pages 23–24. Advantageously, this acceptor number A is less than 20, in particular less than 18.

It is preferable for the said fluorocarboxylic acid or acid salt to be at least partially (at least 10 mol %), preferably fully, soluble in the medium constituting the reagent.

The solvents which give good results may in particular be solvents of amide type. Among the amides, amides of specific nature are also included, such as tetrasubstituted ureas including cyclic tetrasubstituted ureas, in particular 5- or 6-membered ureas, for example DMPU (dimethylpropylenylurea or 1, 3-dimethyl-3, 4, 5, 6-tetrahydro-2(1H)pyrimidinone) and DMEU (dimethylethylenylurea), or 1, 3-dimethyl-2-imidazolidinone and monosubstituted lactams. The amides are preferably substituted (disubstituted for ordinary amides). Examples which may be mentioned are pyrrolidone derivatives, such as N-methylpyrrolidone, or alternatively N,N-dimethylformamide or N, N-dimethylacetamide.

Solvents such as 1,3-dimethyl-3,4,5,6-tetrahydro-2(1H) pyrimidinone (DMPU) or benzonitrile are also advantageous.

Another particularly advantageous category of solvents consists of ethers, whether these are symmetrical or unsymmetrical ethers and whether or not they are open. The various glycol ether derivatives such as the various glymes, for example diglyme, should also be incorporated into the category of ethers.

In the fluorocarboxylic acid of the constituent a) of the reagent of the invention, the species Ew which exerts an electron-withdrawing effect on the difluoro carbon atom is preferably selected from functional groups whose Hammett constant $\sigma_p$ is at least equal to 0.1. It is moreover preferable for the inductive component of $s_p$, $s_i$, to be at least equal to 0.2, advantageously to 0.3. In this respect, reference will be made to the book by March, "Advanced Organic Chemistry", third edition, John Wiley and Son, pages 242 to 250, and in particular to Table 4 of this section.

More particularly, the electron-withdrawing species may be selected from halogen atoms, preferably light ones, in particular chlorine and fluorine. The corresponding fluorocarboxylic acid is a halofluoroacetic acid of formula (1) X—$CF_2$—COOH where X is a halogen atom, advantageously a light one (chlorine or fluorine).

Ew may also be advantageously selected from nitrile (with the risk, as a side reaction, of an a-elimination), carbonylated, sulphonated and perfluoro-alkyled groups. Fluorocarboxylic acids of this type which may be used correspond to the formula (2) R—G—$CF_2$—COOH where R-G represents a nitrile group or alternatively G represents

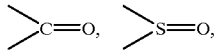

or —$(CF_2)_n$— where n is greater than or equal to 1, and R represents, without discrimination, an organic or even an inorganic residue, preferably an organic radical such as aryl, alkyl or aralkyl, which is optionally substituted. R may also represent an organic solid support, such as a resin, or an inorganic solid support.

In the case where G represents a perfluoro-alkylene group —$(CF_2)_n$—, n is advantageously between 1 and 10, preferably between 1 and 5. Still in this case, R may also represent a halogen atom, in particular fluorine.

In general, except in the case where the fluoro-carboxylic acid is a polymer, the total number of carbon atoms in the fluorocarboxylic acid advantageously does not exceed 50.

The counter-cations capable of forming a salt with the said fluorocarboxylic acid are advantageously bulky. Thus, alkali metal salts, advantageously those in which the alkali metal is selected from sodium, potassium, rubidium, caesium or francium, are preferred. Preferably, the said metal is from a period at least equal in rank to that of sodium, advantageously to that of potassium. Quaternary ammonium salts are also preferred.

It is also possible to improve the reaction by using cations which are either naturally bulky, such as quaternary ammonium cations or quaternary phosphonium cations, or which are rendered bulky by the addition of chelating agents or preferably cryptands, such as, for example, crown ethers or derivatives which are both aminated and oxygenated.

The chelating or sequestering agents which may thus be used are advantageously selected, on the one hand, from amines and, on the other hand, from ethers whose molecules contain at least one other ether function.

Thus, the sequestering agents which may be used are advantageously selected such that they contain either at least one amine function, or alternatively an ether function and at least one amine and/or ether function in order to form a complexing agent which is advantageously at least bidentate, preferably tridentate, the ether and/or amine functions being separated by at least 1 atom, advantageously 2 atoms and by not more than 4 atoms, advantageously not more than 3 atoms, these generally being carbon atoms.

When the carbon atoms supposed to provide the coordination are connected together by 2 branches thus forming a ring, it is preferable for at least one branch to be at least 3-membered, advantageously 4-membered, and for the other branch to be at least 2-membered, advantageously 3-membered.

The bulk and the mobility should be such that the bi-, tri- or polydentate agents are complexing. Such is not the case with 1,4-diazabicyclo(2.2.2.)octane.

In general, this constraint may be quantified by showing that the bicyclic systems obtained by bridging of a ring (which are in fact tricyclic), and which are at most 8-membered, especially when the bridgeheads are the atoms providing the coordination, of the diazabicyclo-octane, -heptane and lower type and, to a lesser extent, -nonane, should be avoided.

More generally, it is advantageous to avoid any bicyclic system:
whose bridgeheads are atoms intended to provide the coordination and
2 branches of which have, not taking the bridgeheads into account, a chain length of not more than 2, preferably of not more than 3 when the third branch is less than 7-membered in length.

The at least bidentate nature with preferably at least one amine function is necessary for phosgene and derivatives, but not for oxalyl halide and equivalents.

At least 3 classes of complexing agents may be mentioned as being particularly interesting comprising: oxygen-containing tertiary amines, oxygen-containing or sulphur-containing polyethers, which can be cyclic or macrocyclic; cryptands.

The first class consists of sequestering agents of general formula:

$$N\text{—}[\text{—}CHR_1\text{—}CHR_2\text{—}O\text{—}(CHR_3\text{—}CHR_4\text{-}O)_n\text{—}R_5]_3 \quad (I)$$

in which n is an integer greater than or equal to 0 and less than or equal to about 10 (0<n<10), $R_1$, $R_2$, $R_3$ and $R_4$, which may be identical or different, represent a hydrogen atom or an alkyl radical having from 1 to 4 carbon atoms and $R_5$ represents an alkyl or cycloalkyl radical having from 1 to 12 carbon atoms, a phenyl radical or a radical of formula —$C_mH_{2m}C_6H_5$, or $C_mH_{2m+1}$—$C_6H_5$, m being between 1 and about 12.

The second class of complexing agents consists of cyclic, preferably macrocyclic, polyethers having from 6 to 30 atoms in the ring and preferably from 15 to 30 atoms in the ring and consisting of 2 to 10, preferably of 4 to 10, units —O—X— in which X is either —$CHR_6$—$CHR_7$— or —$CHR_6$—$CHR_8$—$CR_9R_7$, $R_6$, $R_7$, $R_8$ and $R_9$, which may be identical or different, being a hydrogen atom or an alkyl radical having from 1 to 4 carbon atoms, it being possible for one of the Xs to be —$CHR_6$—$CHR_8$—$CR_9R_7$— when the units —O—X— comprise the group —O—$CHR_6$—$CHR_7$.

The third class of completing agents consists of the compounds described in patent application EP 0,423,008, page 3, line 29 to page 6, line 45.

Perfluorocarboxylic acid salts may advantageously be used, such as the trifluoroacetate, perfluoropropionate and perfluorobutyrate of an alkali metal, in particular potassium.

It is noted that the use of sequestering agents of the crown ether type, in solvents which are relatively non-polar (less polar than DMF), markedly accelerates the conversion of the starting fluorocarboxylic acid.

Such sequestering agents may advantageously be used in a proportion of from 5 to 100 mol %, in particular from 5 to 25 mol %, relative to their initial fluorocarboxylic acid content.

However, certain combinations with the other partners of the reaction medium, in particular certain solvents, may have a less favourable effect as regards the stability of the product formed, and will thus not be considered as being advantageous.

Another aim of the present invention is to provide a process for the synthesis of an organic derivative containing a difluoromethylene group, which uses the reagent according to the present invention.

This aim is achieved:
a) by placing the said reagent together with a compound containing at least one electrophilic function, and
b) by heating the resulting mixture to a temperature of between 100° C. and 200° C., preferably of between 110 and 150° C., for a period of at least half an hour, advantageously of at least one hour, and of not more than one day, advantageously of less than 20 hours.

Still another aim of the present invention is to provide a process for the synthesis of oxysulphide-containing and fluorine-containing organic derivatives, especially of sulphinic or sulphonic acid salts, using the reagent according to the present invention.

This aim is achieved by:
a) exposing the said reagent to an oxide of sulphur and
b) heating the resulting mixture at a temperature of between 100° C. and 200° C., preferably of between 120 and 150° C., and this, for a period of at least half an hour, advantageously of at least one hour, and of at most one day, advantageously of less than 20 hours.

The placing of the reagent together with or in contact with the substrate may or may not be gradual. In particular, it is possible to wait until one of the two is at the right temperature in order to introduce the other. This introduction may or may not be gradual. The reagent may be poured into the substrate or vice versa. The fluorocarboxylate and the substrate may be introduced into the solvent both simultaneously and gradually.

When the said oxide is sulphur dioxide, the mixture resulting from step a) may comprise two phases in equilibrium and may thus contain a liquid phase, where at least part of the said acid or of the sulphur dioxide is dissolved in the said solvent, in equilibrium with a gaseous phase which contains sulphur dioxide.

As regards the relative quantities of the said initial fluorocarboxylic acid, and of oxide of sulphur, preferably dioxide, it is preferable that the ratio is between 1 and 10, advantageously around two, sulphur atoms per molecule of fluordcarboxylic acid.

The reagent of the invention reacts according to the invention with an electrophilic compound, containing an electrophilic atom, it being possible for this atom to be a carbon atom or a hetero atom, for example sulphur, selenium or tellurium. It advantageously reacts with hydrocarbon compounds on an electrophilic carbon atom not belonging to an aromatic system.

According to a first aspect of the invention, the reagent preferably reacts with compounds containing an electrophilic atom, advantageously an electrophilic hetero atom, linked to a halogen atom or to a pseudohalogen group in order to achieve the substitution of the said halogen or pseudohalogen in a single step.

The reaction works proportionately better, in contrast with an SN2 reaction, when it passes via a reaction intermediate originating from an addition onto a multiple bond or onto a doublet.

When the electrophilic atom is a sulphur atom, mention may be made of the reaction with:

the halo or pseudohalo derivatives of organosulphur compounds, in particular sulphenyl, sulphinyl or sulphonyl halides, in which the halogen atom or the pseudohalogen group is substituted during the reaction with a substituted difluoromethyl group;

disulphides, for example optionally substituted aryldisulphides, in which the S—S bond is broken and replaced by a substituted difluoromethyl group; suitable disulphides may in particular be $C_5$–$C_{10}$ aryl disulphides, optionally substituted with a $C_1$–$C_{10}$ alkyl, $C_1$—$C_{10}$ alkoxy or nitro group or with one or more (£ 3) halogen atom(s);

compounds of thiocyanate type in which the cyano group is substituted during the reaction with a substituted difluoromethyl group; preferred thiocyanates are $C_5$–$C_{10}$ aryl thiocyanates, including alkylaryl thiocyanates, and $C_1$–$C_{10}$ alkyl thiocyanates, including aralkyl thiocyanates.

In the above compounds, the halogen atom may be selected from iodine, bromine, chlorine and fluorine atoms. A "pseudohalogen" group is a group which, when leaving, in anionic form, has an associated acid whose pKa is less than 4, preferably less than 3, in particular less than 0.

Groups whose associated acid has an acidity (measured by the Hammett constant) at least equal to that of acetic acid, advantageously to that of sulphonic acids, or trihalo acids, are preferred. One of the typical pseudohalogens is a perfluoroalkanesulphonyloxy group which releases a perfluoroalkanesulphonate. Preferred pseudohalogen groups may be selected from the tosylate (p-toluenesulphonyloxy), mesylate (methanesulphonyloxy), trifluoromethanesulphonyloxy or trifluoroacetoxy group. The acetate group may also be considered as such a leaving group.

According to a second aspect, the reagent also reacts advantageously with a compound selected from carbonyl compounds of ketone, aldehyde, acid halide, activated ester or anhydride type, by performing an addition on the carbonyl function. Preferred and non-limiting examples which may be mentioned are aromatic aldehydes, preferably $C_5$–$C_{10}$ aldehydes, in which the aromatic ring may optionally be substituted with a $C_1$–$C_{10}$ alkyl, $C_1$–$C_{10}$ alkoxy or nitro group or with a halogen atom; cyclic ketones such as cyclohexanone; non-enolizable ketones activated with a donor group, such as trifluoromethylacetophenone; aromatic anhydrides, such as benzoic anhydride.

When there is a risk of reaction between the substrate and the fluorocarboxylate, it may then be preferable to introduce the substrate or the fluorocarboxylate only under conditions of decarboxylation of the said carboxylate (see the above implementation conditions).

The reaction product is generally an alcohol in this case (for example in alkoxide form), the carbon atom of which bearing the hydroxyl function is substituted with a substituted difluoromethyl group. This product may optionally react subsequently with the reagent or with the starting material according to the reaction conditions.

In general, the amount of reagent employed in the process of the invention will be set in a manner known per se according to the functionality of the electrophilic compound.

It should be pointed out that the product derived from the decomposition of the fluorocarboxylic acid may react with itself if it contains one of the functions liable to react, such as those mentioned above.

It may be noted that compounds, in liquid form, containing an electrophilic function are capable of being used as solvent according to the present invention, provided that they are aprotic. The reaction of the present invention may thus be advantageously performed by placing together a) a fluorocarboxylic acid salt as defined above with b) a compound containing at least one electrophilic function acting both as solvent and as reaction substrate.

When using the reagent according to the invention with a substrate containing at least one electrophilic function, it is important that the latter substrate disrupts the conditions described above as little as possible.

Thus, it is preferable to use a sufficiently dehydrated substrate, or one which neither contains acidic hydrogen which may be removed out by strong bases nor contains harmful impurities, that is to say, in general, a substrate which satisfies the same constraints as those outlined for the reagent.

It has been possible to observe that, all factors being otherwise equal, the yield of the intended organic derivative depends on the degree of progress of the reaction and that a very low final yield may be obtained despite a considerable level of conversion of the reagents. Without wishing to be linked to any particular scientific theory, it appears that everything takes place as if there were formation kinetics and degradation kinetics for the products obtained.

In order to avoid an excessive degradation of the final product, and thus to ensure good selectivity of the reaction, it is preferable not to seek to convert the starting fluorocarboxylic acid completely. The progress of the reaction may be controlled by the rate of conversion (DC) of the acid, which is the molar ratio of the amount of acid consumed to the initial amount of acid in the reaction medium, this rate being readily calculated after assay of the acid remaining in the medium.

Advantageously, the reaction will only be carried out until a degree of conversion of 40 to 80%, preferably of 50 to 70%, is produced, and the reaction products will then be separated. It is thus possible to achieve a selectivity of the order of 80% expressed by the desired product/converted fluorocarboxylic acid molar ratio.

In order to be within optimum reaction conditions, it is possible to limit the rate of conversion by acting at the same time on the duration of the reaction, the nature of the solvent and the presence of additives which have a tendency to limit this conversion, for example such as fluoride ions. The reaction kinetics depend, in addition, on the reaction partners (fluorocarboxylic acid and electrophilic reagent) and the appropriate reaction time may readily be adapted to each individual case as a function of these kinetics.

In the case of sulphur dioxide, a reaction time of 2 to 7 hours may be sufficient, depending on the reagent used.

Once the desired rate of conversion has been achieved, the reaction mixture may be treated in a manner which is known per se in order to separate out the product obtained, it being possible for the starting materials to be recycled in order to produce an additional amount of the intended organic derivative.

An additional chemical reaction which allows the desired product to be converted into a more volatile and readily distilled derivative may, if necessary, be carried out for the separation.

When the reagent is reactive with sulphur dioxide, the product obtained by heating the reagent is a sulphinic acid or a sulphinic acid salt whose counterion is that of the starting fluorocarboxylic acid salt.

To separate the reaction product, one advantageous possibility consists in carrying out an additional conversion to a relatively volatile and easily distillable derivative.

Thus, for example, during the reaction between $SO_2$ and the trifluoroacetic acid $CF_3CO_2H$ or its salts, the trifluoromethylsulphinic acid $CF_3SO_2H$ or its salts which are obtained can be easily converted in the presence of chlorine $Cl_2$ to the acid chloride corresponding to an oxidation, namely $CF_3SO_2Cl$ (this is a general reaction for the acids used and especially for the perfluoroalkane-suiphinic acids $R_fSO_2H$). This reaction, which does not affect the reagent based on trifluoroacetic acid, makes it possible advantageously to separate $CF_3SO_2Cl$ by distillation, leaving inorganic chlorides as well as the trifluoromethylation reagent intact in the reaction medium, which can therefore be reused in order to continue the reaction with the oxide of sulphur. This reaction is common to the different fluorine-containing sulphinic acids which can be obtained according to the invention. This example can be generalized to the separation of all types of fluorine-containing oxysulphide-containing organic derivatives obtained according to the invention which are capable of being converted by an appropriate reaction to more volatile products.

To pass from the sulphinic acid to the corresponding sulphonic acid, the reaction product or the purified reaction product should be subjected to an oxidation, which is known per se, especially by means of hydrogen peroxide or sodium hypochlorite. A process for the purification of sodium trifluoromethylsulphinate, and for oxidation to the sulphonate, which is applicable according to the invention, is described in the European patent application published under the number EP-A-0,396,458.

The sulphinic or sulphonic acid salts thus obtained can be converted to the corresponding free acids in an acid medium.

The reaction products, salts or free acids, can be easily isolated and used in subsequent organic synthesis steps. Thus, for example, it is possible to enhance the value of the sulphinyl chlorides obtained from fluorine-containing sulphinic acids prepared according to the invention.

The examples which follow illustrate the invention.

EXAMPLE 1

Synthesis of 1-trifluoromethylbenzyl Alcohol

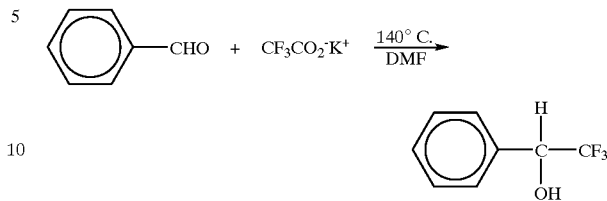

4.98 g (32.7 mmol) of potassium trifluoroacetate and 2 g (18.8 mmol) of benzaldehyde are mixed together in 26 g of anhydrous DMF, under a nitrogen atmosphere.

The molar ratio of the trifluoroacetate to the benzaldehyde is 1.7.

The mixture obtained is transferred to a 50 ml Hastelloy reactor. Once the reactor is closed, the mixture is heated at 104° C. for 3 h 30.

After cooling to 5° C., the reaction crude is drawn off, diluted in $CH_2Cl_2$ and washed with water.

The organic phase is dried and then assayed by gas chromatography.

The rate of conversion (RC) of the benzaldehyde is 50% (in terms of number of moles of benzaldehyde converted relative to the initial number of moles of benzaldehyde) and the actual yield (AY) of 1-trifluoromethylbenzyl alcohol is 20%.

EXAMPLE 2

The reaction between potassium trifluoroacetate and benzaldehyde is carried out as in Example 1, replacing the DMF by NMP (N-methylpyrrolidone).

7.6 g of $CF_3CO_2^-K^+$ (50 mmol) and 3.2 g of benzaldehyde (30 mmol) are dissolved in 40 g of NMP.

The water content of the medium is less than 4 mol % relative to the trifluoroacetate.

The mixture is heated at 140° C. for 3 h 30.

The processing and assay of the reaction crude performed as in Example 1 gives

Rate of conversion of the benzaldehyde=55%

Yield of 1-trifluoromethylbenzyl alcohol=15%

EXAMPLE 3

The reaction between potassium trifluoroacetate and benzaldehyde is carried out as in Example 1, the DMF being replaced by acetonitrile. 2 g of benzaldehyde and 4.75 g of potassium trifluoroacetate are dissolved in 25 ml of $CH_3CN$.

The mixture is heated at 140° C. for 3 h 30.

After processing and assay of the reaction crude, the following are obtained

Rate of conversion of the benzaldehyde=53%

Yield of 1-trifluoromethylbenzyl alcohol=2.5%

The main product formed in this reaction is cinnamonitrile (Z and E isomers).

Cinnamonitrile is formed by condensation of the anion of acetonitrile with benzaldehyde, followed by dehydration.

This example shows that the solvent to be used should not have excessively acidic protons.

EXAMPLE 4

The reaction between potassium trifluoroacetate (5.05 g; 32.7 mmol) and para-fluorobenzaldehyde (2.5 g; 20.2 mmol) in 25 ml of DMF is performed under the conditions of Example 1.

The mixture is heated at 140° C. for 4 h 00.

After processing, gas chromatographic (GC) assay gives

RC p-fluorobenzaldehyde=75%

AY 1-trifluoromethyl(p-fluorobenzyl) alcohol £ 2%

The main product corresponds to the addition of the intermediate trifluoromethyl carbinolate formed with the para-fluorobenzaldehyde:

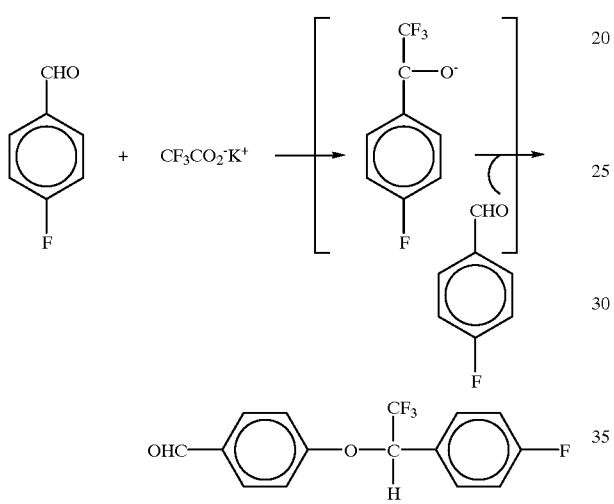

This reaction shows that when the electrophile used contains several reactive functions, side reactions may take place.

EXAMPLE 5

A mixture consisting of 1.43 g of $CF_3CO_2^-K^+$ (9.44 mmol) and 0.55 g of cyclohexanone (5.6 mmol) diluted in 6.4 g of DMF is heated at 140° C. for 5 h 30. GC analysis of the reaction crude after hydrolysis gives

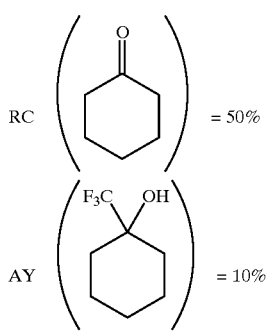

The main products formed correspond to the products of condensation of cyclohexanone with itself followed by a dehydration:

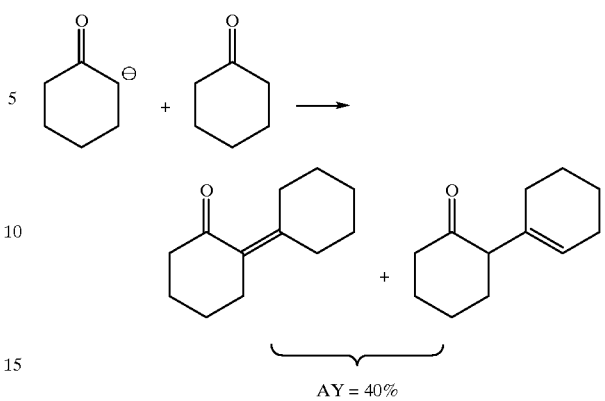

AY = 40%

This reaction shows that when the electrophile possesses an enolizable function, side reactions may take place.

EXAMPLE 6

Reaction of Trifluoromethylacetophenone with $CF_3CO_2K$.

A mixture of $CF_3CO_2^-K^+$ (0.87 g; 5.7 mmol) and 0.62 g (3.56 mmol) of trifluoromethylacetophenone dissolved in 6.5 g of DMF is heated at 140° C. for 5 h 30.

After cooling and hydrolysis, GC analysis of the reaction medium gives

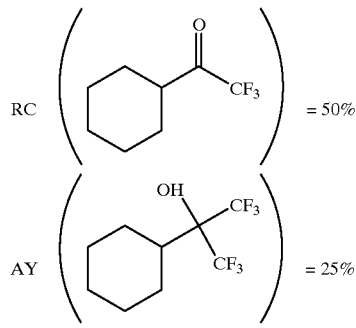

The same reaction may be performed in NMP instead of DMF.

EXAMPLE 7

Reaction Between Benzoic Anhydride and Potassium Trifluoroacetate

A mixture of 0.81 g (5.32 mmol) of $CF_3CO_2^-K^+$ and 0.7 g (3.1 mmol) of benzoic anhydride in 6.15 g of NMP is heated at 140° C. for 5 h 30. After hydrolysis, GC analysis of the reaction medium gives RC (($\Phi$CO)$_2$O) = 100%

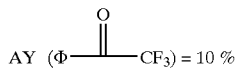

-continued

AY (Φ—C(OH)(CF$_3$)—CF$_3$) = 20 %

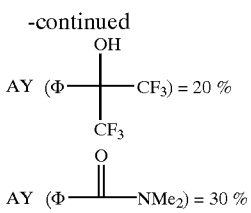

AY (Φ—C(O)—NMe$_2$) = 30 %

Bis (trifluoromethyl) carbino

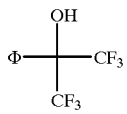

comes from the trifluoromethylation of the trifluoromethylacetophenone intermediately formed:

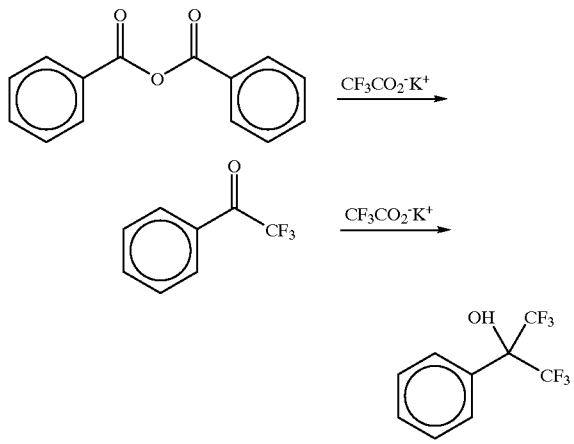

N,N-Dimethylbenzamide originates from a reaction of the degradation of DMF which produces N,N-dimethyl-amine, the latter reacting with benzoic anhydride:

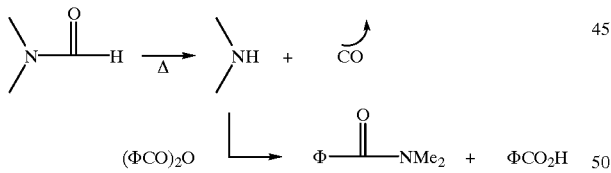

The reaction between benzoic anhydride and CF$_3$CO$_2^-$K$^+$ may also be carried out in DMF.

EXAMPLE 8

Reaction Between Diphenyl Disulphide C$_6$H$_5$SSC$_6$H$_5$ and CF$_3$CO$_2^-$K$^+$.

A mixture of 0.83 g (5.46 mmol) of CF$_3$CO$_2^-$K$^+$ and 0.6 g (2.75 mmol) of diphenyl disulphide in 6.2 g of DMF is heated at 140° C. for 6 h 00.

Analysis of the reaction medium (after hydrolysis) by GC and $^{19}$F NMR gives

RC (C$_6$H$_5$SSC$_6$H$_5$)=67%

AY (C$_6$H$_5$SCF$_3$)=84%.

The reaction may be carried out in the same way in NMP.

COUNTER-EXAMPLE

Working as in Example 8, but with an additional 20 mol % of CuI added relative to the initial CF$_3$CO$_2^-$K$^+$(5.46 mmol), total inhibition of the trifluoromethylation reaction of diphenyl disulphide is obtained.

EXAMPLE 9

Reaction Between Bis(4-nitrophenyl) Disulphide and CF$_3$CO$_2^-$K$^+$.

Repeating the procedure of Example 8 with a mixture of 0.82 g (5.39 mmol) of CF$_3$CO$_2^{-K+}$ and 0.83 g (2.7 mmol) of bis(4-nitrophenyl) disulphide in 7 g of DMF, a reaction crude also containing, besides the starting bis(4-nitrophenyl) disulphide, 4-nitrothiofluoromethylbenzene is obtained

EXAMPLE 10

Reaction of Benzyl Thiocyanate C$_6$H$_5$CH$_2$SCN with CF$_3$CO$_2^-$K$^+$.

A mixture of 0.67 g (4.45 mmol) of CF$_3$CO$_2^-$K$^+$ and 0.42 g (2.8 mmol) of benzyl thiocyanate in 5 g of DMF is heated at 140° C. for 3 h 00.

After hydrolysis, GC analysis of the reaction crude gives:

RC (C$_6$H$_5$—CH$_2$SCN)=100%

AY (C$_6$H$_5$—CH$_2$SCF$_3$)=36%

The reaction may be carried out in a similar manner in NMP.

The results presented in the following examples are expressed as a function of three parameters which are defined below:
- the rate of conversion of a reagent R (RCR) is the ratio of the molar quantity of R which has disappeared during a reaction over the initial quantity of R;
- the actual yield of production of a product P from a reagent R (RYP) is the ratio of the quantity of P produced over the initial quantity of R;
- the yield of conversion of R to P (YCP) which is the ratio of the quantity of P produced over the quantity of R which has disappeared.

EXAMPLE 11

Preparation of Trifluoromethylsulphinic Acid 42 g of N-methylpyrrolidone (NMP) are introduced into a 100 ml Hastalloy reactor, stirred by a turbine, followed by 5.32 g (35 mmol) of potassium trifluoroacetate and finally 4.9 g (76 mmol) of sulphur dioxide gas by bubbling in the liquid. The sulphur dioxide is completely solubilized by the NMP.

The molar ratio of the sulphur dioxide to the potassium trifluoroacetate is 2.1.

The water content of the reactive mixture is 0.1% by weight relative to the weight of the mixture, that is to say a molar ratio of water to trifluoroacetate of 0.07.

The mixture is heated in the closed reactor at a temperature of 140° C. for 6 hours, with stirring.

During the reaction, the internal pressure of the reactor, expressed in terms of room temperature, increases by 3.5'·10$^5$ Pa relative to the initial pressure.

The reaction medium is then taken up in water and analysed by ionic chromatography HPIC (High Performance Ionic Chromatography) in separating mode in order to determine the conversion of the potassium trifluoroacetate.

The rate of conversion (RC) of the starting potassium trifluoroacetate, expressed by the molar ratio of the quantity of trifluoroacetate consumed (converted) to the initial quantity, is 61.7%.

The actual yield (AY), expressed by the molar ratio of the quantity of trifluoromethylsulphinate formed, in free or salified form, to the initial quantity of trifluoroacetate, is 29.7%.

The yield relative to the converted product (YC), expressed by the molar ratio of the quantity of trifluoromethylsulphinate formed, in free or salified form, to the quantity of trifluoroacetate converted, is 48.1%. The product is isolated in the form of a potassium salt.

EXAMPLE 12

Example 11 is repeated exactly, except that 8.6 g (35 mmol) of caesium trifluoroacetate are used in the reagent.

The HPIC assay makes it possible to calculate that RC is equal to 68.4%, RY is equal to 21% and YC is equal to 30.7%. The product is isolated in the form of a caesium salt.

The use of caesium trifluoroacetate is relatively less advantageous than the potassium salt.

EXAMPLES 13 and 14

Example 11 is repeated exactly, except that N,N-dimethylacetamide (DMAC, e=37.8) and N,N-dimethylformamide (DMF, $\epsilon$=36.7) are used as solvent, respectively.

The progress of the reaction is determined by HPIC and the results are reported in Table 1, where the solvent used and its donor number D are stated as a reminder, for each example.

COMPARATIVE EXAMPLE 1

Example 11 is repeated exactly, except that the procedure is carried out only in the presence of an excess of sulphur dioxide without solvent (dielectric constant $\epsilon$=14).

The results are presented in Table 1.

TABLE 1

| Example | Solvent | DN | RC | RY | YC |
|---|---|---|---|---|---|
| Ex 1 | NMP | 27.3 | 61.7 | 29.7 | 48.1 |
| Ex 3 | DMAC | 27.8 | 78.6 | 40.6 | 51.7 |
| Ex 4 | DMF | 26.6 | 80.4 | 33.8 | 41.7 |
| Comp Ex 1 | — (SO$_2$)* | — | 9 | 0 | 0 |

*SO$_2$ serves both as solvent and reagent.
The Comparative Example 1 shows that the solvent is necessary for the conversion to the desired product.

EXAMPLE 15

This example summarizes a series of other tests where various solvents were tested under conditions similar to those of Example 11.

The potassium trifluoroacetate (in a CF$_3$CO$_2$K/solvent weight ratio=0.13) is exposed to about 2 molar equivalents of sulphur dioxide (SO$_2$/CF$_3$CO$_2$K molar ratio of 1.9 to 2.1).

The mixture of reagents is heated in a closed reactor stirred at 1000 rpm with a temperature rise of 10° C./min up to 140° C., for 6 h.

The progress of the reaction is determined by HPIC and the results are presented in Table 2 where the solvent used, its dielectric constant $\epsilon$, its donor number DN, its acceptor number AN and the water content in the medium are stated as a reminder for each test.

TABLE 2

| Test | Solvent | $\epsilon$ | DN | AN | H$_2$O/CF$_3$CO$_2$K mol % | RC (%) | AY CF$_3$SO$_2$K (%) | AY F$^-$ (%) | YC CF$_3$SO$_2$K (%) |
|---|---|---|---|---|---|---|---|---|---|
| a | DMSO | 48.9 | 29.8 | 19.3 | 4 | 26.6 | 4.6 | — | 17.3 |
| b | CH$_3$CN | 38 | 14.1 | 18.3 | 1.6 | 12.6 | 3 | 3 | 23.8 |
| c | DMF | 36.7 | 26.6 | 16.0 | 1 | 73.5 | 41.8 | 10.9 | 56.9 |
| d | NMP | 32.2 | 27.3 | 13.3 | 1.6 | 67.2 | 27.9 | 25.1 | 41.5 |
| e | Benzonitrile | 25.2 | 11.9 | 15.5 | 1.5 | 22.1 | 7.4 | 3.6 | 33.5 |
| f | DMPU | 36.1 | / | / | 1.5 | 82.1 | 42.9 | 9.8 | 52.3 |
| g | DMAC | 37.8 | 27.8 | 13.6 | 1.9 | 74 | 43.4 | 3 | 58.6 |
| h | Anisole | 4.3 | / | / | 1.2 | 21.6 | 4.4 | 3 | 20.4 |
| i | Xylene | 2.4 | / | / | 0.4 | 23.2 | 4.4 | 3 | 19 |
| j | Diglyme | 5.7 | / | 9.9 | 1.9 | 28.4 | 15.6 | 3 | 54.9 |
| k | DMI (DMEU) | 37.6 | / | / | 1.4 | 66.1 | 47.5 | 7.4 | 72 |

In general, for the solvents which are not very acidic (AN<19), the yields vary in the same direction as the dielectric constant $\epsilon$. In this regard, the DMF, DMAC and DMPU give excellent results, those of NMP being slightly lower.

On the other hand, with DMSO and CH$_3$CN, the results are less good, in spite of high dielectric constants, and this is caused by their acidic character (AN=19.3).

EXAMPLE 16

Example 11 is repeated exactly, except that more carefully dehydrated reactive compounds are used. The water content in the reactive mixture is 0.05% by weight relative to the weight of the mixture, that is to say a water to trifluoroacetate molar ratio of 0.04. The results of the test, determined by HPIC, are presented in Table 3. The results of Example 11 are also given in the Table as a reminder.

COMPARATIVE EXAMPLE 2

(To Be Compared with Examples 11 and 16)

In contrast to the preceding example, Example 11 is repeated with more hydrated reagents, such that the content of releasable protons is outside the limits of the invention. The water content in the reactive mixture is 0.8% by weight relative to the weight of the mixture. The water to trifluoroacetate molar ratio is 0.6, the ratio of the content of releasable protons provided by the water to the content of trifluoroacetate is therefore 1.2. The results of the test, determined by HPIC, are presented in Table 3.

EXAMPLE 17

Example 16 is repeated exactly, except that DMAC is used as solvent.

The results of the test are presented in Table 3, where the results of Example 13 are also presented.

TABLE 3

| Example | $H_2O$ (% by weight) | $H_2O/CF_3COOK$ (mol/mol) | RC (%) | RY (%) | YC (%) |
|---|---|---|---|---|---|
| Ex 11 | 0.1 | 0.07 | 61.7 | 29.7 | 48.1 |
| Ex 16 | 0.05 | 0.04 | 64 | 54 | 85 |
| Comp Ex 2 | 0.8 | 0.6 | 100 | 0 | 0 |
| Ex 13 | 0.1 | 0.07 | 78.6 | 40.6 | 51.7 |
| Ex 17 | 0.05 | 0.04 | 68 | 47 | 69 |

Examples 16 and 17 show that a low water content remarkably enhances the yield of conversion.

The Comparative Example 12 confirms that a releasable proton content of the reactive system greater than half the content of trifluoroacetic acid salt is detrimental to the reaction for the formation of the trifluoromethylsulphinate.

EXAMPLE 18

This example summarizes a series of tests which also demonstrate the importance of the water content in the reaction of the sulphur dioxide with the potassium trifluoroacetate under conditions similar to those of Example 11.

Still in NMP, the potassium trifluoroacetate (in a weight ratio relative to the solvent $CF_3CO_2K/NMP=0.13$) is exposed to about 2 molar equivalents of sulphur dioxide ($SO_2/CF_3CO_2K$ molar ratio of 1.9 to 2.1).

The mixture is heated in the closed reactor stirred at 1000 rpm with a temperature rise of 10° C./min up to 140° C. for 6 hours.

The results are summarized in the following Table 4:

TABLE 4

| Test | $H_2O/CF_3COOK$ (% mol) | RC $CF_3CO_2K$ (%) | AY $CF_3SO_2K$ (%) | YC $CF_3SO_2K$ (%) |
|---|---|---|---|---|
| a | 1.9 | 67.2 | 27.9 | 41.5 |
| b | 2.3 | 64.2 | 43.2 | 67.3 |
| c | 3.9 | 65.3 | 44.2 | 67.6 |
| d | 6.9 | 69.4 | 39.6 | 57.1 |
| e | 8.9 | 69.1 | 39.9 | 57.7 |

In these tests, the formation of fluoride ions is observed with an AY yield of about 25%.

A marked improvement in the yield and the selectivity is observed on passing from conditions a) to b) An optimum appears within the range from 2 to 8%, around 4%.

EXAMPLE 19

This example summarizes a series of tests where fluoride ions were introduced into the reaction medium from the beginning of the reaction.

Test 9.a was carried out in NMP according to the procedure of Example 15, test d, and by adding 1 mole of potassium fluoride per mole of starting trifluoro-carboxylic acid.

Tests 9.b–d were carried out in DMF according to the procedure of test 5.c and by adding various quantities of KF.

Tests 9.e, f, g were carried out in the same solvents using, this time, caesium fluoride.

The results are presented in the following Table 5:

TABLE 5

| Test | Solvent | Fluoride $F^-/CF_3CO_2K$ mol % | $H_2O/CF_3CO_2K$ mol % | RC $CF_3CO_2K$ % | AY $CF_3SO_2K$ % | YC $CF_3SO_2K$ |
|---|---|---|---|---|---|---|
| 5.d | NMP | 0 | 1.7 | 67.1 | 27.9 | 41.5 |
| 9.a | " | KF 100 | 0.9 | 54.1 | 39.1 | 72.3 |
| 5.c | DMF | 0 | 1 | 73.5 | 41.8 | 56.9 |
| 9.b | " | KF 100 | 2 | 63.4 | 44.3 | 70 |
| 9.c | " | KF 10 | 1.4 | 73.8 | 45.9 | 62.2 |
| 9.d | " | KF 1 | 1.7 | 76 | 44.8 | 58.9 |
| 9.e | NMP | CSF 100 | | 57.7 | 37.4 | 64.8 |
| 9.f | " | CSF 10 | 1.3 | 67.2 | 42.9 | 63.8 |
| 9.g | DMF | CSF 100 | 1.9 | 62.6 | 46.2 | 73.8 |

In all cases, the rate of conversion of $CF_3CO_2K$ is limited by the presence of the fluorides and an increase is observed in the selectivity and, in general, the yields.

EXAMPLE 20

In this example, the results obtained in the absence and in the presence of a sequestering crown ether, 18-crown-6, are compared.

Different tests were performed in various solvents, according to the procedure of Example 16.

The results are summarized in the following table.

TABLE 6

| Test | Solvent | $H_2O/CF_3CO_2K$ (mol %) | 18 Cr6/$CF_3CO_2K$ (mol %) | RC (%) | AY $CF_3SO_2K$ (%) | YC $F^-$ (%) | YC $CF_3SO_2K$ (%) |
|---|---|---|---|---|---|---|---|
| 5.d | NMP | 1.9 | 0 | 67.2 | 27.9 | 25.1 | 41.5 |
| 10.a | NMP | 1.5 | 25 | 73.8 | 23.8 | 0 | 32.2 |
| 5.b | $CH_3CN$ | 1.6 | 0 | 12.6 | 3 | 3 | 23.8 |
| 10.b | $CH_3CN$ | 1.5 | 25 | 47.6 | 6.1 | 3 | 12.8 |
| 5.e | Benzonitrile | 1.5 | 0 | 22.1 | 7.4 | 3.6 | 33.5 |
| 10.c | Benzonitrile | 1.2 | 25 | 35.8 | 14.8 | 5.7 | 41.3 |
| 5.i | Xylene | 0.5 | 0 | 23.2 | 4.4 | 3 | 19 |
| 10.d | Xylene | 0.5 | 25 | 28.4 | 6.3 | 3 | 22.2 |

In all cases, the conversion of the starting product is favoured, without notable effect, however, on the decomposition into fluorides. This is even reduced with the NMP solvent.

In tests b, c and d, the real yield of $CF_3SO_2K$ is much better when the sequestrant is used.

EXAMPLE 21

This example presents a kinetic study of the reaction of test 5.d.

The rate of conversion of the trifluoroacetate, the real yield and the yield of conversion of the trifluoromethylsulphinate as well as the real yield of fluoride ion were determined for reaction times varying between 2 and 9h 30 min.

The results are summarized in Table 7 below.

TABLE 7

| Test | Time (h) | $H_2O/CF_3C$— $O_2K$ mol % | RC % | RY $CF_3SO_2K$ % | RY $F^-$ % | YC $CF_3SO_2K$ % |
|---|---|---|---|---|---|---|
| 11.a | 2 | 1.3 | 46.2 | 23.5 | 3 | 51 |
| 11.b | 4 | 1.2 | 52.7 | 42.1 | 3 | 79.9 |
| 5.d | 6 | 1.9 | 67.2 | 27.9 | 25.1 | 41.5 |
| 11.c | 9 h 30 min | 1.3 | 31.4 | 4.1 | 83.3 | 5 |

A maximum yield and a maximum selectivity are observed at around 4 h of reaction.

When the reaction time increases, the yield drops and an increasing quantity of fluoride ions appears, which is a sign of degradation of the trifluoromethyl groups in the medium.

EXAMPLE 22

Preparation of Pentafluoroethyl-sulphinic Acid 40 g of NMP, 7.07 g of anhydrous $C_2F_5COOK$ (35 mmol) and 4.9 g (76 mmol) of $SO_2$ are introduced into the same reactor as that of Example 11.

The mixture is heated in the closed reactor at a temperature of 140° C. for 6 hours.

The pressure variation inside the reactor between the beginning and the end of the reaction is 3.5 bar.

The reaction medium is taken up in water and then the mixture is assayed by $^{19}F$ NMR.

The rate of conversion RC is equal to 85%, the actual reaction yield AY is equal to 73% and the yield of conversion YC is equal to 86.2%. The product is isolated in the form of a potassium salt.

EXAMPLE 23

Preparation of Heptafluoropropyl-sulphinic Acid 40 g of NMP, 8.8 g of anhydrous $C_3F_7COOK$ (35 mmol) and then 4.9 g (76 mmol) of $SO_2$ are introduced into the same reactor as that of Example 11.

The mixture is heated in the closed reactor at a temperature of 140° C. for 1 h 30 min.

The pressure variation inside the reactor between the beginning and the end of the reaction is 4.5 bar.

The reaction medium is taken up in water, then the mixture is assayed by $^{19}F$ NMR.

The rate of conversion RC is equal to 85%, the actual reaction yield AY is equal to 70% and the yield of conversion YC is equal to 82%.

The product is isolated in the form of a potassium salt.

EXAMPLE 24

Preparation of Trifluoromethyl-sulphinyl Chloride

Potassium trifluoromethylsulphinate is prepared under the conditions of Example 14.

The DMF is removed from the reaction mixture by vacuum distillation at a temperature not exceeding 55–60° C.

The distillation residue is taken up in acetonitrile and then filtered. The filtrate is distilled in order to remove the solvent and the potassium trifluoromethylsulphinate is isolated with a purification yield of 96% relative to the crude reaction mixture, assayed by ionic chromatography.

The product resulting from this operation is taken up in toluene and supplemented with thionyl chloride $SOCl_2$ in a stoichiometric quantity relative to the trifluoromethylsulphinate. The trifluoromethyl-sulphinyl chloride ($CF_3SOCl$) is obtained with a yield of 65%.

EXAMPLE 25

Preparation of Trifluoromethylsulphonyl Chloride

Potassium trifluoromethanesulphinate is prepared under the conditions of Example 14.

The DMF is removed from the reaction mixture by vacuum distillation at a temperature not exceeding 60° C.

The distillation residue is taken up in water.

Chlorine is bubbled through the aqueous solution in a stoichiometric quantity relative to the trifluoromethyl sulphinate present in the medium.

The reaction temperature is 0°–5° C.

By separating the bottom layer after settling has taken place, the trifluoromethylsulphonyl chloride is isolated.

This crude product is distilled, b.p.: 28–31° C. The yield is 80% relative to the trifluoromethylsulphinate present in the medium.

EXAMPLE 26

Preparation of Trifluoromethyl-sulphonic Acid (Triflic Acid)

The aqueous solution obtained under the same conditions as those described in Example 25 is oxidized with hydrogen peroxide at 30 volumes. A 10% excess of hydrogen peroxide relative to the potassium trifluoromethyl sulphinate is necessary.

The reaction temperature is 5° C.

After distillation of the water and drying, the salts obtained are acidified using 100% sulphuric acid. The triflic acid is thus separated from the trifluoromethyl acetic acid.

What is claimed is:

1. Nucleophilic reagent which is useful for grafting a substituted difluoromethyl group onto a compound containing at least one electrophilic function, or for the synthesis of oxysulphide-containing and fluorine-containing organic derivatives, wherein said reagent comprises:
    a) a fluorocarboxylic acid of formula Ew—$CF_2$—COOH where Ew represents an electron-withdrawing atom or group, at least partially salified with an organic or inorganic cation, and
    b) a polar aprotic solvent;
wherein an amount of releasable protons of the reagent carried by its various components, including their impurities, is at most equal to half an initial molar concentration of the fluorocarboxylic acid and wherein the reagent does not comprise a transition element having two stable valency states.

2. Reagent according to claim 1, wherein said polar aprotic solvent is the compound containing at least one electrophilic function.

3. Reagent according to claim 1, wherein said amount of releasable protons is at most equal to 10% of the initial molar concentration of the fluorocarboxylic acid salt.

4. Reagent according to claim 1, wherein its water content is less than 10% of the initial molar concentration of the fluorocarboxylic acid.

5. Reagent according to claim 1, wherein an amount of elements from column VIII B of the Periodic Table of the Elements is less than 100 mol ppm, relative to the said fluorocarboxylic acid salt.

6. Reagent according to claim 1, wherein an amount, expressed as equivalents, of ionic fluoride is at most equal to the initial molar concentration of the fluorocarboxylic acid salt.

7. Reagent according to claim 1, wherein the polar aprotic solvent has a donor number between 10 and 30.

8. Reagent according to claim 1, wherein the polar aprotic solvent has an acceptor number less than 20.

9. Reagent according to claim 1, wherein the solvent has a pKa corresponding to the first acidity at least equal to 20.

10. Reagent according to claim 1, further comprising a sequestering crown ether.

11. Reagent according to claim 1, wherein the electron-withdrawing atom or group is chosen from electron-withdrawing groups whose Hammett constant $\sigma_p$ is at least equal to 0.1.

12. Reagent according to claim 1, wherein the fluorocarboxylic acid is chosen from the compounds of formula (1) X—$CF_2$—COOH, where X represents a halogen atom, and the compounds of formula (2) R—G—$CF_2$—COOH, where R—G represents a nitrile group or alternatively G represents C=O, S=O or —$(CF_2)_n$— with n greater than or equal to 1 and R represents, without discrimination, an organic or inorganic residue.

13. Reagent according to claim 1, wherein the fluorocarboxylic acid or an acid salt thereof is fully soluble in a reagent medium.

14. Reagent according to claim 13, wherein the acid salt is a salt of an alkali metal chosen from sodium, potassium, rubidium, caesium and francium, or a quaternary ammonium salt.

15. Reagent according to claim 1, wherein the polar aprotic solvent is chosen from N-disubstituted amides, cyclic or acyclic ethers, and benzonitrile.

16. A nucleophilic reagent which is useful for grafting a substituted difluoromethyl group onto a compound containing at least one electrophilic function, or for the synthesis of oxysulphide-containing and fluorine-containing organic derivatives, wherein said reagent comprises:
    a) a fluorocarboxylic acid of formula Ew-$CF_2$—COOH where Ew represents an electron-withdrawing atom or group, at least partially salified with an organic or inorganic cation,;
    b) a polar aprotic solvent; and
    b) a sequestering crown ether;
wherein an amount of releasable protons of the reagent carried by its various components, including their impurities, is at most equal to half an initial molar concentration of the fluorocarboxylic acid and wherein the reagent does not comprise a transition element having two stable valency states.

17. Reagent according to claim 1 wherein the polar aprotic solvent is selected from the group consisting of amide solvents, tetrasubstituted urea solvents, cyclic tetrasubstituted urea solvents, 5-membered urea solvents, 6-membered urea solvents, dimethylpropylenylurea (DMPU) solvents, 1,3-dimethyl-3,4,5,6-tetrahydro-2 (1H) pyrimidinone solvents, dimethylethylenylurea (DMEU) solvents, 1,3-dimethyl-2-imidazolidinone solvents, mono-substituted lactam solvents, substituted amide solvents, disubstituted amide solvents, pyrrolidone derivatives solvents, 1,3-dimethyl-3,4,5,6-tetrahydro-2 (1H) pyrimidinone (DMPU) solvents, benzonitrile solvents, ether solvents, glycol ether derivatives solvents, glyme solvents, and diglyme solvents.

* * * * *